(12) United States Patent
Tsai et al.

(10) Patent No.: US 9,802,208 B2
(45) Date of Patent: Oct. 31, 2017

(54) CENTRIFUGAL ROTOR WITH ARC-SHAPED CENTRIFUGAL CARRIER OR WEIGHT BODY

(75) Inventors: Chung-Hsien Tsai, Hsinchu County (TW); Hsiao-Chung Tsai, Taoyuan County (TW); Ying-Lan Tsai, New Taipei (TW)

(73) Assignee: PROTECTLIFE INTERNATIONAL BIOMEDICAL INC., Taipei (TW)

( * ) Notice: Subject to any disclaimer, the term of this patent is extended or adjusted under 35 U.S.C. 154(b) by 322 days.

(21) Appl. No.: 14/350,811

(22) PCT Filed: Oct. 10, 2011

(86) PCT No.: PCT/CN2011/001693
§ 371 (c)(1),
(2), (4) Date: Apr. 10, 2014

(87) PCT Pub. No.: WO2013/053077
PCT Pub. Date: Apr. 18, 2013

(65) Prior Publication Data
US 2014/0296050 A1  Oct. 2, 2014

(51) Int. Cl.
*B01L 3/00* (2006.01)
*G01N 35/00* (2006.01)
*B04B 7/00* (2006.01)
*B04B 5/04* (2006.01)

(52) U.S. Cl.
CPC ............... *B04B 7/00* (2013.01); *B01L 3/5027* (2013.01); *G01N 35/00069* (2013.01);
(Continued)

(58) Field of Classification Search
CPC ....... B04B 5/04; B04B 5/0407; B04B 5/0428; B04B 5/0442; B04B 7/00;
(Continued)

(56) References Cited

U.S. PATENT DOCUMENTS

| 5,242,606 A * | 9/1993 | Braynin ................ B01L 3/5021 210/380.1 |
| 2005/0109686 A1* | 5/2005 | Hawes ...................... B04B 5/02 210/198.2 |

(Continued)

FOREIGN PATENT DOCUMENTS

| WO | WO 2011088582 A1 * | 7/2011 | ............... B01L 3/502 |
| WO | WO 2012120463 A1 * | 9/2012 | ............. G01N 21/07 |

*Primary Examiner* — Charles Cooley
*Assistant Examiner* — Shirley S Liu
(74) *Attorney, Agent, or Firm* — CKC & Partners Co., Ltd.

(57) ABSTRACT

A centrifugal rotor includes a support disk and a centrifugal carrier. The centrifugal carrier is assembled within the support disk. The centrifugal carrier includes an arc-shaped body, a sample application chamber, a sample metering chamber, a diluent chamber, a diluent metering chamber, a metering control member and a mixing chamber. The sample metering chamber is communicated with the sample application chamber. The sample metering chamber is positioned radially outward from the sample application chamber. The diluent metering chamber is communicated with the diluent chamber. The diluent metering chamber is positioned radially outward from diluent chamber. The metering control member is slidingly connected within or detachably fixed to the sample metering, chamber or the diluent metering chamber. The mixing chamber is communicated with the diluent metering chamber and the sample metering chamber respectively. The mixing chamber is positioned radially outward from both the diluent metering chamber and the sample metering chamber.

10 Claims, 4 Drawing Sheets

(52) U.S. Cl.
CPC ... *B01L 2200/025* (2013.01); *B01L 2200/028* (2013.01); *B01L 2200/0605* (2013.01); *B01L 2300/0816* (2013.01); *B01L 2300/0867* (2013.01); *B01L 2400/0409* (2013.01); *B04B 5/04* (2013.01); *B04B 5/0407* (2013.01); *G01N 2035/00158* (2013.01)

(58) Field of Classification Search
CPC .... G01N 35/00069; G01N 2035/00158; B01L 2200/025; B01L 2200/028; B01L 2200/0605; B01L 2300/0816; B01L 2300/0867; B01L 2400/0409; B01L 3/5027
USPC .............................. 494/5, 10, 23, 27, 28, 30
See application file for complete search history.

(56) References Cited

U.S. PATENT DOCUMENTS

| | | | | |
|---|---|---|---|---|
| 2006/0091085 | A1* | 5/2006 | Kobayashi | B01L 3/50273 210/787 |
| 2010/0290955 | A1* | 11/2010 | Cho | B01L 3/502753 422/506 |
| 2011/0020196 | A1* | 1/2011 | Grippi | A61B 17/00491 422/535 |
| 2011/0120580 | A1* | 5/2011 | Takahashi | B01J 19/0093 137/797 |
| 2012/0202673 | A1* | 8/2012 | Runyon | G01N 33/80 494/37 |

* cited by examiner

CENTRIFUGAL ROTOR WITH ARC-SHAPED CENTRIFUGAL CARRIER OR WEIGHT BODY

CROSS-REFERENCE TO RELATED APPLICATIONS

This application is a continuation of International application No. PCT/CN2011/001693, filed on Oct. 10, 2011, the contents of which is incorporated herein by reference.

BACKGROUND

Field of Invention

The present invention relates to a centrifugal rotor. More particularly, the present invention relates to a centrifugal rotor in biochemical and haulm logical analyses.

Description of Related Art

Biological analysis of blood and other specimen usually require quickly distributing liquid to perform different tests. Biochemical analysis also requires cell bodies and body fluids to be separated prior to testing to prevent from being influenced by each other. The distributing step and separation step are usually achieved by a centrifugation step, and then be manually or automatically assigned to the quantity of each sample specimen vessel. The above quantitative allocation process is not only laborious but also time-consuming. Thus, a variety of automated specimen quantitative distribution systems have been proposed to improve these labor-consuming processes.

At present, the main distribution system improvement is the use of automated quantitative centrifugal rotor. After these centrifugal rotors are used with centrifuges, quantitative distribution of the specimen, sample mixing and diluting can be performed for optical analysis purposes. Although there are already several centrifugal rotor designs, more effort is still needed to enhance the convenience and precision of performing the biochemical analysis.

Therefore, inconvenience and defects still exist in the structure and use of a conventional centrifugal rotor, and need to be further improved. In order to solve the above problems, all the venders think hard to seek a solution, but it seems that no product can effectively solve the above problems. Accordingly, how to create a new type of centrifugal rotor is one of the currently important research topics, but also become the industry improvement goals in urgent needs.

SUMMARY

It is therefore an objective of the present invention to provide an improved centrifugal rotor.

In accordance with the foregoing and other objectives of the present invention, a centrifugal rotor includes a support disk and at least one centrifugal carrier. The at least one centrifugal carrier is assembled within the support disk. The centrifugal carrier includes an arc-shaped body, a sample application chamber, a sample metering chamber, a diluent chamber, a diluent metering chamber, a metering control member and a mixing chamber. The sample application chamber is located on the arc-shaped body. The sample metering chamber is located on the arc-shaped body and communicated with the sample application chamber. The sample metering chamber is positioned radially outward from the sample application chamber. A diluent chamber is located on the arc-shaped body. The diluent metering chamber is located on the arc-shaped body and communicated with the diluent chamber. The diluent metering chamber is positioned radially outward from diluent chamber. The metering control member is slidingly connected within the sample metering chamber or the diluent metering chamber. The mixing chamber is located on the arc-shaped body and communicated with the diluent metering chamber and the sample metering chamber respectively. The mixing chamber is positioned radially outward from both the diluent metering chamber and the sample metering chamber.

In order deal with the objectives of the present invention and its technical problems, the following technical features can be further implemented.

According to another embodiment disclosed herein, a volume of the metering control member is half, one third or one fourth of a volume of diluent metering chamber, and a volume of the metering control member is half, one third or one fourth of a volume of the sample metering chamber.

According to another embodiment disclosed herein the centrifugal rotor further includes at least one weight body assembled within the support disk.

According to another embodiment disclosed herein, the centrifugal rotor further includes an excess sample dump and an excess diluent dump, the excess sample dump is located on the arc-shaped body and communicated with the sample metering chamber, the excess sample dump is positioned radially outward from the sample metering chamber, the excess diluent dump is located on the arc-shaped body and communicated with the diluent metering chamber, the excess diluent dump is positioned radially outward from the diluent metering chamber.

According to another embodiment disclosed herein, the centrifugal rotor further includes a mixing metering chamber located on the arc-shaped body and communicated with the mixing chamber, the mixing metering chamber is positioned radially outward from the mixing chamber.

In accordance with the foregoing and other objectives of the present invention, another centrifugal rotor includes a support disk and at least one centrifugal carrier. The at least one centrifugal carrier is assembled within the support disk. The centrifugal carrier includes an arc-shaped body, a sample application chamber, a sample metering chamber, a diluent chamber, a diluent metering chamber, a metering control member and a mixing chamber. The sample application chamber is located on the arc-shaped body. The sample metering chamber is located on the arc-shaped body and communicated with the sample application chamber. The sample metering chamber is positioned radially outward from the sample application chamber. A diluent chamber is located on the arc-shaped body. The diluent metering chamber is located on the arc-shaped body and communicated with the diluent chamber. The diluent metering chamber is positioned radially outward horn diluent chamber. The metering control member is detachably fixed to the sample metering chamber or the diluent metering chamber. The mixing chamber is located on the arc-shaped body and communicated with the diluent metering chamber and the sample metering chamber respectively. The mixing chamber is positioned radially outward from both the diluent metering chamber and the sample metering chamber.

In order deal with the objectives of the present invention and its technical problems, the following technical features can be further implemented.

According to another embodiment disclosed herein, a volume of the metering control member is half, one third or one fourth of a volume of diluent metering chamber, and a volume of the metering control member is half, one third or one fourth of a volume of the sample metering chamber.

According to another embodiment disclosed herein, the centrifugal rotor further includes an excess sample dump and an excess diluent dump, the excess sample dump is located on the arc-shaped body and communicated with the sample metering chamber, the excess sample dump is positioned radially outward from the sample metering chamber, the excess diluent dump is located on the arc-shaped body and communicated with the diluent metering chamber, the excess diluent dump is positioned radially outward from the diluent metering chamber.

According to another embodiment disclosed herein, the centrifugal rotor further includes a mixing metering chamber located on the arc-shaped body and communicated with the mixing chamber, the mixing metering chamber is positioned radially outward from the mixing chamber.

According to another embodiment disclosed herein a gap is formed between the metering control member and a surrounding inner wall of the sample metering chamber or the diluent metering chamber when the metering control member is fixed to the sample metering chamber or the diluent metering chamber.

According to another embodiment disclosed herein, the centrifugal rotor further includes at least one weight body assembled within the support disk.

The present invention has the following advantages and benefits compared with the prior art. The centrifugal carrier disclosed herein is equipped with a metering control member to be installed within the sample metering chamber or the diluent metering chamber to adjust the sample metering chamber or the diluent metering chamber, thereby providing different mixing ratios of biological sample to diluents. As using the plastic injection molding to manufacture the centrifugal carrier is concerned, the metering control member reduces the cost of manufacturing a new injection mold. When a new centrifugal carrier needs a different ratio of the sample metering chamber to the diluent metering chamber, only a metering control member is needed to be installed into the sample metering chamber or the diluent metering chamber without manufacturing a new injection mold.

Thus, it is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1A:
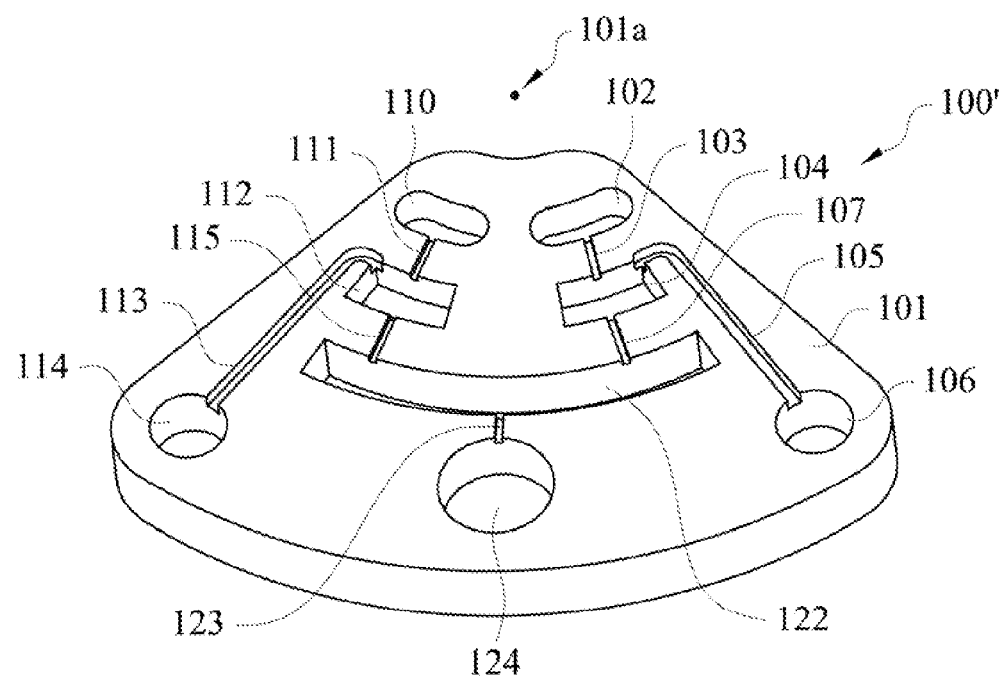
FIG. 1A illustrates a centrifugal carrier according to an embodiment of this invention.

Reference will now be made in detail to the present embodiments of the invention, examples of which are illustrated in the accompanying drawings. Wherever possible, the same reference numbers are used in the drawings and the description to refer to the same or like parts.

Figure 1B:
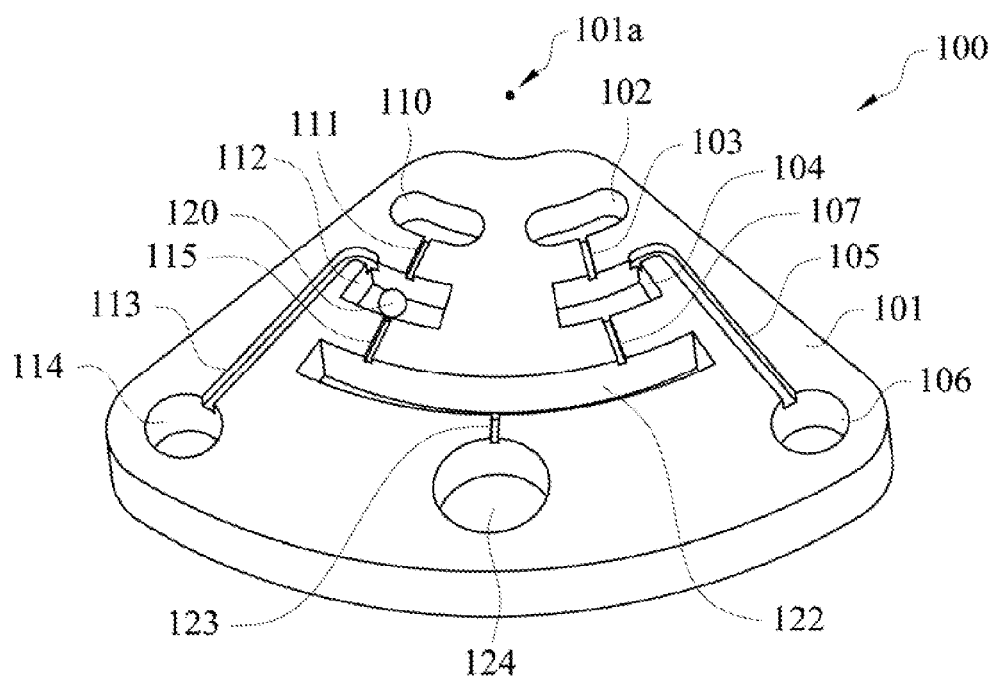
FIG. 1B illustrates the centrifugal carrier in FIG. 1A with a metering control member added.

Referring to FIG. 1A and FIG. 1B, FIG. 1A illustrates a centrifugal carrier according to an embodiment of this invention, and FIG. 1B illustrates the centrifugal carrier in FIG. 1A with a metering control member added. A centrifugal carrier 100 should be used in a centrifuge and biochemical analysis device (not shown in the drawings) for filling and distributing biochemical sample. The centrifugal carrier 100 has an arc-shaped body 101. The arc-shaped body 101 has an arc rim, which is part of a circle, and the arc-shaped body 101 has a center 101a. The arc-shaped body 101 as illustrated in FIGS. 1A and 1B is part, e.g., one fourth and one fifth, of a circular disk, and persons skilled in the art can add the remaining parts according to actual demands. In this embodiment, the arc-shaped body 101 has a sample application chamber 102 and a diluent chamber 110, which are both closer to the center 101a. The biological sample, e.g. blood, can be manually deposited into the sample application chamber 102. The diluent chamber 110 is used to be filled by diluents or a diluent container.

The sample metering chamber 104 is located on the arc-shaped body 101 and communicated with the sample application chamber 102 via a delivery channel 103. The sample metering chamber 104 should be positioned radially outward from the sample application chamber 102, e.g., being farther from the center 101a of the arc-shaped body, such that the sample metering chamber 104 receives fluid from sample application chamber 102 when the arc-shaped body 101 is used under centrifugal force.

The diluent metering chamber 112 is located on the arc-shaped body 101 and communicated with the diluent chamber 110 via a delivery channel 111. The diluent metering chamber 112 should be positioned radially outward from the diluent chamber 110, i.e., being farther from the center 101a of the arc-shaped body, such that the diluent metering chamber 112 receives fluid from the diluent chamber 110 when the arc-shaped body 101 is used under centrifugal force.

The sample metering chamber 104 and the diluent metering chamber 112 are used to determine a mixing ratio of biological sample to diluents. In this embodiment, a metering control member 120, e.g., a ball, is located within the sample metering chamber 104 or the diluent metering chamber 112 to adjust an inner volume of the sample metering chamber 104 or the diluent metering chamber 112 so as to provide more mixing ratios of biological sample to diluents. In this embodiment, the metering control member 120 is slidingly connected within the sample metering chamber 104 or the diluent metering chamber 112. Since the metering control member 120 is not fixed within the sample metering chamber 104 or the diluent metering chamber 112, it would not stop fluid flowing. As using the plastic injection molding to manufacture the centrifugal carrier is concerned, the metering control member reduces the cost of manufacturing a new injection mold. In other words, when a new centrifugal carrier needs a different ratio of the sample metering chamber 104 to the diluent metering chamber 112, only a metering control member 120 is needed to be installed into the sample metering chamber 104 or the diluent metering chamber 112 without manufacturing a new injection mold.

A volume of the metering control member 120 can be half, one third, one fourth or other ratios of a volume of diluent metering chamber 112. A volume of the metering control member 120 can also be half, one third, one fourth or other ratios of a volume of the sample metering chamber 104.

The mixing chamber 122 is positioned radially outward from both the sample metering chamber 104 and the diluent metering chamber 112, and communicated with the sample metering chamber 104 via a delivery channel 107 and communicated with the diluent metering chamber 112 via a delivery channel 115. When the arc-shaped body 101 is used under centrifugal force, the mixing chamber 122 receives fluid from both the sample metering chamber 104 and the diluent metering chamber 112.

In addition, the mixing chamber 122 may has its mixing metering chamber 124 for metering a mixed solution to be analyzed. The mixing metering chamber 124 is communicated with the mixing chamber 122 via a delivery channel 123, and the mixing metering chamber 124 is positioned radially outward from the mixing chamber 122, i.e., being farther from the center 101a of the arc-shaped body.

An excess sample dump 106 is communicated with the sample metering chamber 104 via a delivery channel 105, and the excess sample dump 106 is positioned radially outward from the sample metering chamber 104, i.e., being farther from the center 101a of the arc-shaped body. Therefore, when the arc-shaped body 101 is used under centrifugal force, excess biological sample, i.e., more than a capacity of the sample metering chamber 104, is driven into the excess sample dump 106.

An excess diluent dump 114 is communicated with the diluent metering chamber 112 via the delivery channel 113, and the excess diluent dump 114 is positioned radially outward from the diluent metering chamber 112, i.e., being farther from the center 101a of the arc-shaped body. Therefore, when the arc-shaped body 101 is used under centrifugal force, excess diluents, i.e., more than a capacity of the diluent metering chamber 112, are driven into the excess diluent dump 114.

Figure 2A:
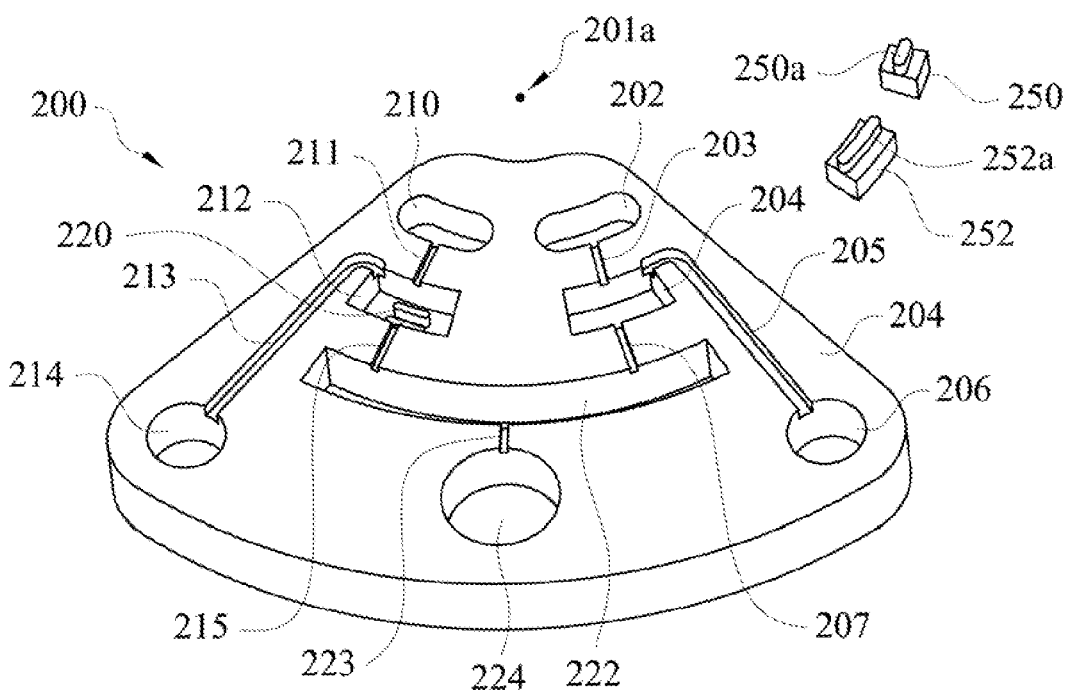
FIG. 2A illustrates a centrifugal carrier according to another embodiment of this invention.
Figure 2B:
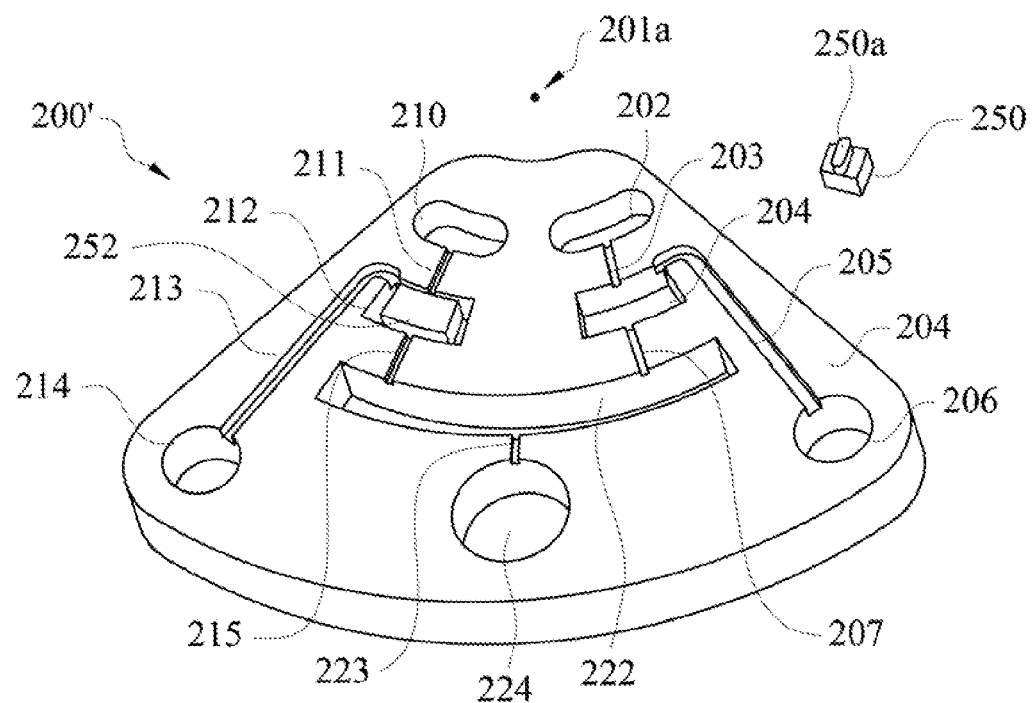
FIG. 2B illustrates the centrifugal carrier in FIG. 2A with a metering control member added.

Retelling to FIG. 2A and FIG. 2B, FIG. 2A illustrates a centrifugal carrier according to another embodiment of this invention, and FIG. 2B illustrates the centrifugal carrier in FIG. 2A with a metering control member added. The centrifugal carrier 200 is different from the centrifugal carrier 100 in that the metering control member is detachably fixed to the sample metering chamber or the diluent metering chamber (i.e., the metering control member cannot be slid at will).

A centrifugal carrier 200 has an arc-shaped body 201. The arc-shaped body 201 has an arc rim, which is part of a circle, and the arc-shaped body 201 has a center 201a. The arc-shaped body 201 as illustrated in FIGS. 2A and 2B is part, e.g., one fourth and one fifth, of a circular disk, and persons skilled in the art can add the remaining parts according to actual demands. In this embodiment, the arc-shaped body 201 has a sample application chamber 202 and a diluent chamber 210, which are both closer to the center 201a. The biological sample, e.g. blood, can be manually deposited into the sample application chamber 202. The diluent chamber 210 is used to be filled by diluents or a diluent container.

The sample metering chamber 204 is located on the arc-shaped body 201 and communicated with the sample application chamber 202 via a delivery channel 203. The sample metering chamber 204 should be positioned radially outward from the sample application chamber 202, i.e., being farther from the center 201a of the arc-shaped body, such that the sample metering chamber 204 receives fluid from sample application chamber 202 when the arc-shaped body 201 is used under centrifugal force.

The diluent metering chamber 212 is located on the arc-shaped body 201 and communicated with the diluent chamber 210 via a delivery channel 211. The diluent metering chamber 212 should be positioned radially outward from the diluent chamber 210, i.e., being farther from the center 101a of the arc-shaped body, such that the diluent metering chamber 212 receives fluid from the diluent chamber 210 when the arc-shaped body 201 is used under centrifugal force.

The sample metering chamber 204 and the diluent metering chamber 212 are used to determine a mixing ratio of biological sample to diluents. In this embodiment, metering control members (250, 252) are located within the sample metering chamber 204 or the diluent metering chamber 212 to adjust an inner volume of the sample metering chamber 204 or the diluent metering chamber 212 so as to provide more mixing ratios of biological samples to diluents. In this embodiment, the metering control members (250, 252) are detachably fixed to the sample metering chamber 204 or the diluent metering chamber 212. That is, the metering control members (250, 252) are unmovable (cannot be slid) after they are fixed to the sample metering chamber 204 or the diluent metering chamber 212. The metering control members (250,252) are equipped with position members (250a, 252a) to engage a position member 220 of the diluent metering chamber 212. The sample metering chamber 204 may also be equipped with position members. As using the plastic injection molding to manufacture the centrifugal carrier is concerned, the metering control member reduces the cost of manufacturing a new injection mold. In other words, when a new centrifugal carrier needs a different ratio of the sample metering chamber 204 to the diluent metering chamber 212, only metering control members (250, 252) are needed to be installed into the sample metering chamber 204 or the diluent metering chamber 212 without manufacturing a new injection mold. When the metering control members (250, 252) are secured to the sample metering chamber 204 or the diluent metering chamber 212, a gap is formed between the metering control member (250, 252) and a surrounding inner wall of the sample metering chamber 204 or the diluent metering chamber 212 to allow the biological samples or diluents to be flowed through. That is the metering control member (250, 252) is in contact with an inner bottom wall of the sample metering chamber 204 or the diluent metering chamber 212 that is closest to the support disk 302, and not in contact with an inner surrounding sidewall of the sample metering chamber 204 or the diluent metering chamber 212, and not in contact with an inner wall of a delivery channel (211, 213, 215, 203, 205, 207) that is communicated with the sample metering chamber 204 or the diluent metering chamber 212 when the metering control member (250, 252) is fixed to the sample metering chamber 204 or the diluent metering chamber 212.

A volume of the metering control member (250, 252) can be half, one third, one fourth or other ratios of a volume of diluent metering chamber 212. A volume of the metering control member (250, 252) can also he half, one third, one fourth or other ratios of a volume of the sample metering chamber 204.

The mixing chamber 222 is positioned radially outward from both the sample metering chamber 204 and the diluent metering chamber 212, and communicated with the sample metering chamber 204 via a delivery channel 207 and communicated with the diluent metering chamber 212 via a delivery channel 215. When the arc-shaped body 201 is used under centrifugal force, the mixing chamber 222 receives fluid from both the sample metering chamber 204 and the diluent metering chamber 212 so as to mix the biological samples and diluents.

In addition, the mixing chamber 222 may has its mixing metering chamber 224 for metering a mixed solution to be analyzed. The mixing metering chamber 224 is communicated with the mixing chamber 222 via a delivery channel 223, and the mixing metering chamber 224 is positioned radially outward from the mixing chamber 222.

An excess sample dump 206 is communicated with the sample metering chamber 204 via a delivery channel 205, and the excess sample dump 206 is positioned radially outward from the sample metering chamber 204. Therefore, when the arc-shaped body 201 is used under centrifugal force, excess biological sample, i.e., more than a capacity of the sample metering chamber 204, is driven into the excess sample dump 206.

An excess diluent dump 214 is communicated with the diluent metering chamber 212 via the delivery channel 213, and the excess diluent dump 214 is positioned radially outward from the diluent metering chamber 212, i.e., being farther from the center 201a of the arc-shaped body. Therefore, when the arc-shaped body 201 is used under centrifugal force, excess diluents, i.e., more than a capacity of the diluent metering chamber 212, are driven into the excess diluent dump 214.

Figure 3:
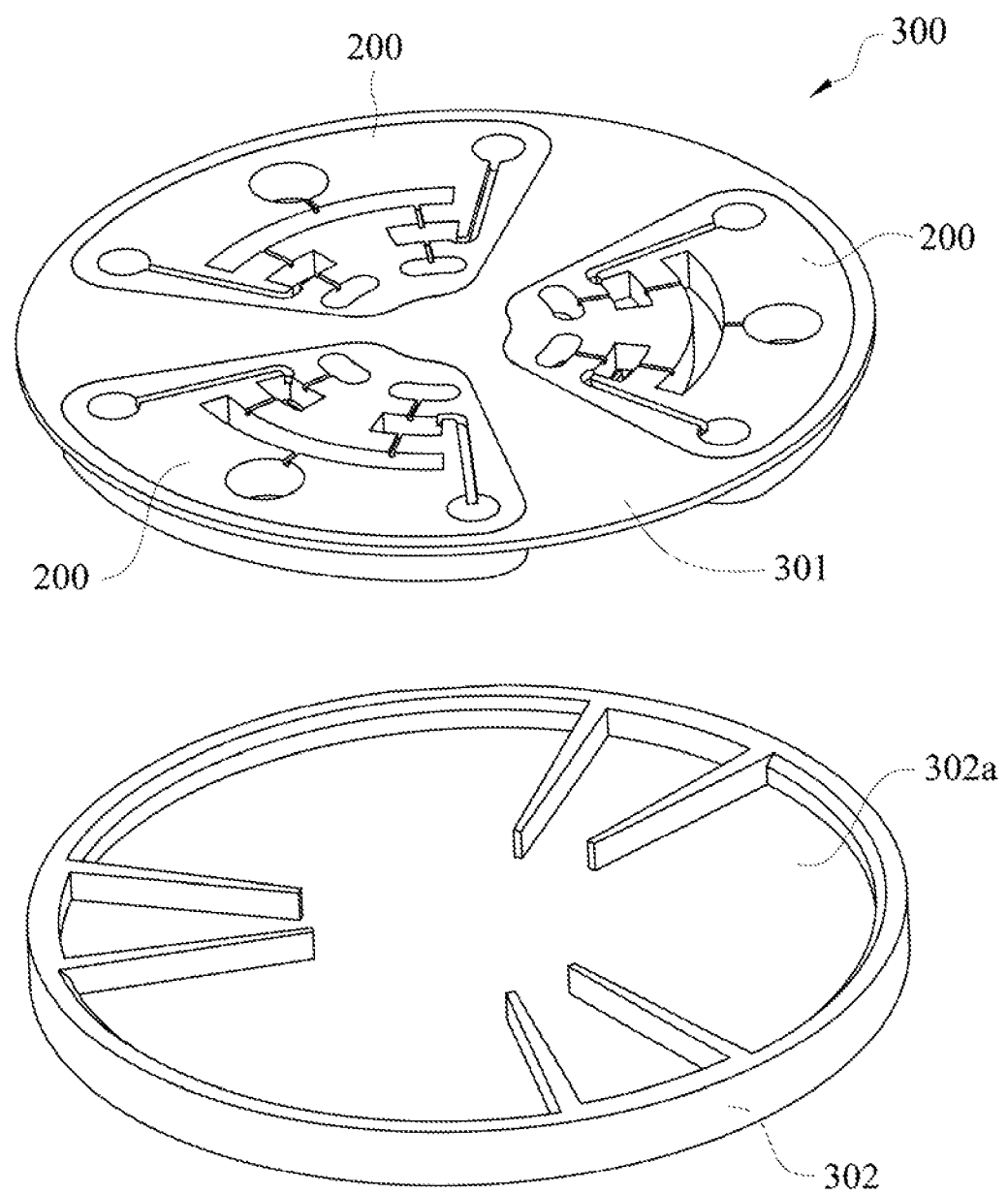
FIG. 3 illustrates an exploded view of a centrifugal rotor according to an embodiment of this invention.

FIG. 3 illustrates an exploded view of a centrifugal rotor according to an embodiment of this invention. The centrifugal rotor 300 includes a support disk 302 and a carrier disk 301. The carrier disk 301 includes a plurality of centrifugal carriers 200, which are assembled to a concave area 302a of the support disk 302. A bottom portion of the support disk 302 is coupled with a centrifuge so as to drive the centrifugal rotor 300 to rotate. The amount of the centrifugal carrier 200 on the support disk 302 is not limited, and several centrifugal carriers 200 can provide different mixing ratios of biological sample to diluents by adding or removing the metering control members. Therefore, a single centrifugal rotor 300 can perform several different biochemical and immunological analyses simultaneously.

Figure 4:
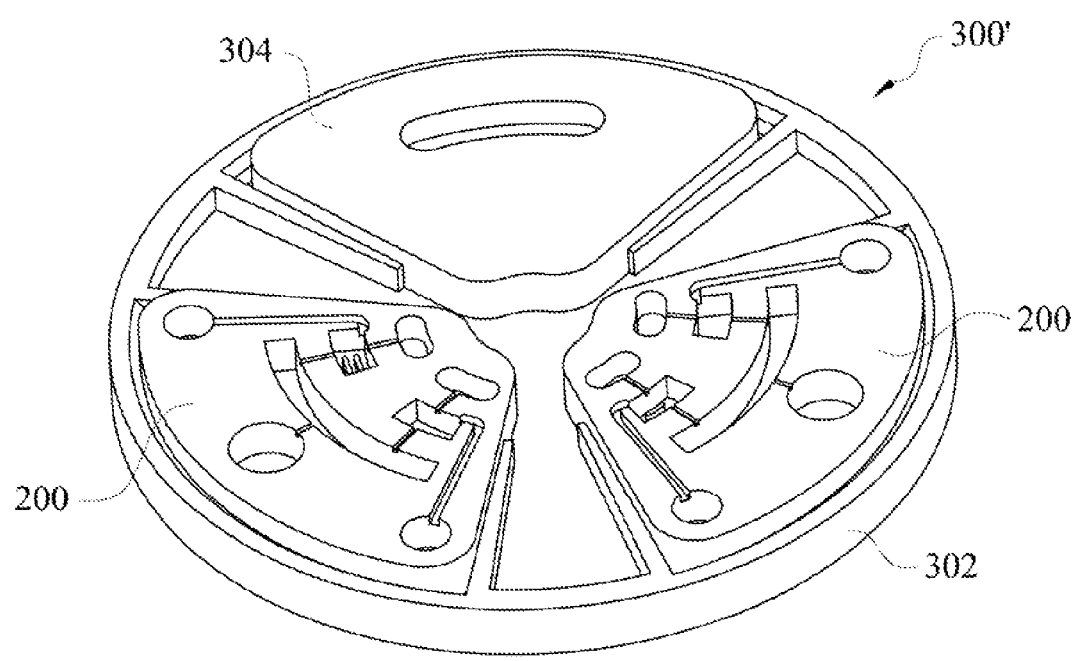
FIG. 4 illustrates a centrifugal rotor in an assembled status according to another embodiment of this invention.

FIG. 4 illustrates a centrifugal rotor 300' in an assembled status according to another embodiment of this invention. In this embodiment, two centrifugal carriers 200 and a weight body 304 are assembled within the support disk 302. The weight body 304 is used to balance the weight on the centrifugal rotor 300' under the centrifugal force such that the centrifugal rotor 300' can be rotated reliably.

Figure 5:
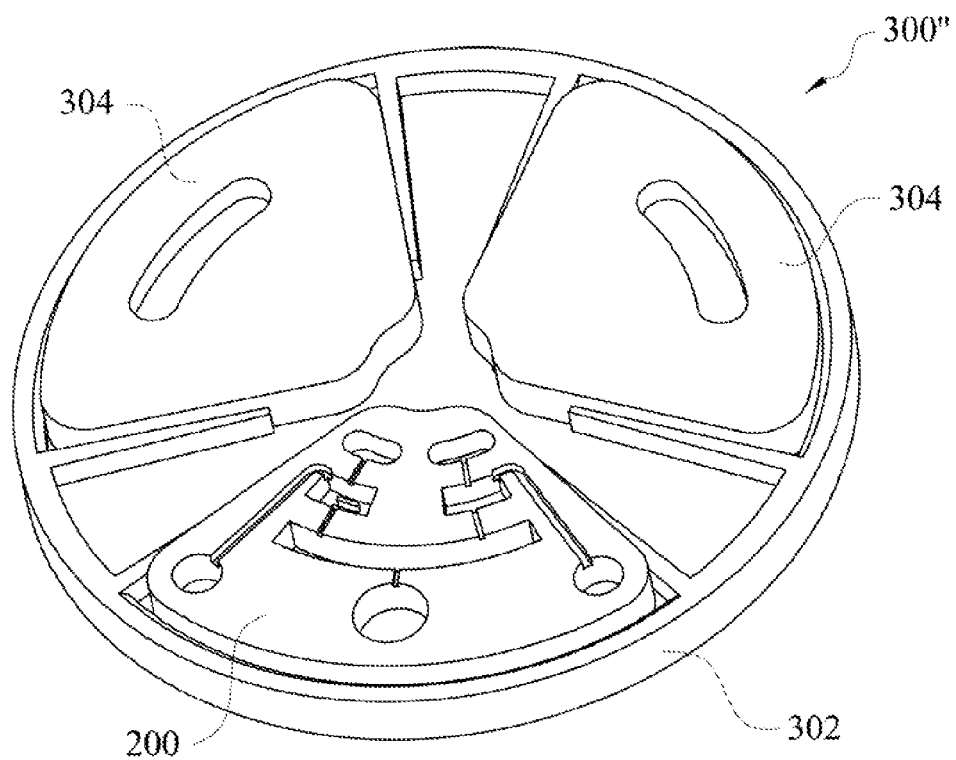
FIG. 5 illustrates a centrifugal rotor in an assembled status according to still another embodiment of this invention.

FIG. 5 illustrates a centrifugal rotor 300" in an assembled status according to still another embodiment of this invention. In this embodiment, a centrifugal carrier 200 and two weight bodies 304 are assembled within the support disk 302. The weight body 304 is used to balance the weight on the centrifugal rotor 300" under the centrifugal force such that the centrifugal rotor 300" can be rotated reliably.

According to the embodiments in FIG. 4 and FIG. 5, the combination of the centrifugal carrier 200, the weight body 304 and the support disk 302 can perform several different biochemical analyses simultaneously at a lowest cost.

According to the above-discussed embodiments, the centrifugal carrier disclosed herein is equipped with a metering control member to be installed within the sample metering chamber or the diluent metering chamber to adjust the sample metering chamber or the diluent metering chamber, thereby providing different mixing ratios of biological sample to diluents. As using the plastic injection molding to manufacture the centrifugal carrier is concerned, the metering control member reduces the cost of manufacturing a new injection mold. When a new centrifugal carrier needs a different ratio of the sample metering chamber to the diluent metering chamber, only a metering control member is needed to be installed into the sample metering chamber or the diluent metering chamber without manufacturing a new injection mold.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A centrifugal rotor comprising:
   a support disk having a plurality of concave areas; and
   a carrier disk assembled within the support disk and haying at least two arc-shaped centrifugal carriers, each arc-shaped centrifugal carrier is assembled within a corresponding one of the plurality of concave areas, wherein each centriftrual carrier comprises:
   an arc-shaped body;
   a sample application chamber disposed on the arc-shaped body;
   a sample metering chamber disposed on the arc-shaped body, and communicated with the sample application chamber, the sample metering chamber being radially outward from the sample application chamber;
   a diluent chamber disposed on the arc-shaped body;
   a diluent metering chamber disposed on the arc-shaped body and communicated with the diluent chamber, the diluent metering chamber being radially outward from diluent chamber;
   a metering control member detachably fixed to and installed inside the sample metering chamber or the diluent metering chamber, wherein the metering control member is in contact with an inner bottom wall of the sample metering chamber or the diluent metering chamber that is closest to the support disk, and not in contact with an inner surrounding sidewall of the sample metering chamber or the diluent metering chamber, and not in contact with an inner wall of a delivery channel that is communicated with the simple metering chamber or the diluent metering chamber when the metering control member is fixed to the sample metering chamber or the diluent metering chamber; and
   a mixing chamber disposed on the arc-shaped body and communicated with the diluent metering chamber and the sample metering chamber respectively, the mixing chamber being radially outward from both the diluent metering chamber and the sample metering chamber.

2. The centrifugal rotor of claim 1, wherein the metering control member occupies half, one third or one fourth of a volume of the diluent metering chamber, and a volume of the metering control member occupies half, one third or one fourth of a volume of the sample metering chamber.

3. The centrifugal rotor of claim 1 further comprising:
   an excess sample dump disposed on the arc-shaped body and communicated with the sample metering, chamber, the excess sample dump being radially outward from the sample metering chamber; and an excess diluent dump disposed on the arc-shaped body and communicated with the diluent metering chamber, the excess diluent dump being radially outward from the diluent metering chamber.

4. The centrifugal rotor of claim 1 further comprising a mixing metering chamber disposed on the arc-shaped body and communicated with the mixing chamber, the mixing metering chamber being radially outward from the mixing chamber.

5. A centrifigal rotor comprising:
a support disk having a plurality of concave areas;
at least one arc-shaped weight body assembled within a corresponding one of the plurality of concave areas; and
at least one centrifugal earner assembled within a corresponding one of the plurality of concave areas, wherein the centrifugal carrier comprises:
an arc-shaped body;
a sample application chamber disposed on the arc-shaped body;
a sample metering chamber disposed on tie arc-shaped body, and communicated with the sample application chamber, the sample metering chamber being radially outward from the sample application chamber;
a diluent chamber disposed on the arc-shaped body;
a diluent metering chamber disposed on the arc-shaped body and communicated with the diluent chamber, the diluent metering chamber being radially outward from diluent chamber;
a metering control member detachably fixed to and installed inside the sample metering chamber or the diluent metering chamber, wherein the metering control member is in contact with an inner bottom wall of the sample metering chamber or the diluent metering chamber that is closest to the support disk, and not in contact with an inner surrounding sidewall of the sample metering chamber or the diluent metering chamber, and not in contact with an inner wall of a delivery channel that is communicated with the sample metering chamber or the diluent metering chamber when the metering control member is fixed to the sample metering, chamber or the diluent metering chamber; and a mixing chamber disposed on the arc-shaped body and communicated with the diluent metering chamber and the sample metering chamber respectively, the mixing chamber being radially outward from both the di hent metering chamber and the sample metering chamber.

6. The centrifugal rotor of claim 5, wherein the metering control member occupies half, one third or one fourth of a volume of the diluent metering chamber, and the metering control member occupies half, one third or one fourth of a volume of the sample metering chamber.

7. The centrifugal rotor of claim 5 further comprising:
an excess sample dump disposed on the arc-shaped body and communicated with the sample metering chamber, the excess sample dump being radially outward from the sample metering chamber; and
an excess diluent dump disposed on the arc-shaped body and communicated with the diluent metering chamber, the excess diluent dump being radially outward from the diluent metering chamber.

8. The centrifugal rotor of claim 5 further comprising a mixing metering chamber disposed on the arc-shaped body and communicated with the mixing chamber, the mixing metering chamber being radially outward from the mixing chamber.

9. The centrifugal rotor of claim 5, wherein the metering control member has a first position member to engage a second position member of the sample metering chamber or the diluent metering chamber so as to fix the metering control member inside the sample metering chamber or the diluent metering chamber.

10. The centrifugal rotor of claim 1, wherein the metering control member has a first position member to engage a second position member of the sample metering chamber or the diluent metering chamber so as to fix the metering control member inside the sample metering chamber or the diluent metering chamber.

* * * * *